United States Patent [19]

Pituch

[11] Patent Number: 5,024,666
[45] Date of Patent: Jun. 18, 1991

[54] MEDICAL NEEDLE SHEATH HOLDING APPARATUS

[76] Inventor: Daniel W. Pituch, 3299 Kennett Sq., Pittsburgh, Pa. 15213

[21] Appl. No.: 408,992

[22] Filed: Sep. 18, 1989

[51] Int. Cl.$^5$ .............................................. A61M 5/32
[52] U.S. Cl. .................... 604/263; 604/192; 206/366
[58] Field of Search ................ 604/110, 192, 263; 206/365-367; 269/24, 156, 265

[56] References Cited

U.S. PATENT DOCUMENTS

| 4,596,562 | 6/1986 | Vernon. | |
|---|---|---|---|
| 4,717,386 | 1/1988 | Simmons. | |
| 4,738,362 | 4/1988 | Burns et al. | 206/366 |
| 4,742,910 | 5/1988 | Staebler. | |
| 4,798,587 | 1/1989 | Willoughby. | |
| 4,801,013 | 1/1989 | Bruno | 206/366 |
| 4,862,573 | 9/1989 | Kelson et al. | 206/366 |
| 4,867,309 | 9/1989 | Germain | 206/366 |
| 4,915,698 | 4/1990 | Levenson | 604/263 |
| 4,917,672 | 4/1990 | Terndrup et al. | 604/192 |

FOREIGN PATENT DOCUMENTS

| 296406 | 12/1988 | European Pat. Off. . | |
|---|---|---|---|
| 94318 | 8/1969 | France | 604/174 |
| 2199497 | 7/1988 | United Kingdom | 604/192 |
| 2205043 | 11/1988 | United Kingdom . | |
| 2215215 | 9/1989 | United Kingdom | 604/110 |

Primary Examiner—Stephen C. Pellegrino
Assistant Examiner—Ralph A. Lewis
Attorney, Agent, or Firm—Clifford A. Poff

[57] ABSTRACT

In accordance with the present invention there is provided an apparatus for permitting an individual to unsheath and resheath the needles of hypodermic syringes, catheters, etc., with the use of only one hand. Consequently, the present invention permits free use of the individual's other hand when such is required, e.g., when restraint of the patient is necessary in order to properly and safely administer an injection from a hypodermic needle or the like. The apparatus securely holds and positions a medical needle sheath during such times that a medical needle is removed from and reinserted into the sheath.

12 Claims, 5 Drawing Sheets

MEDICAL NEEDLE SHEATH HOLDING APPARATUS

BACKGROUND OF THE INVENTION

1. Field of the Invention

The present invention generally relates to medical equipment, and more particularly to apparatus for securely holding the sheath or protective cap of a hypodermic syringe needle, catheter needle, or the like, during removal of the needle from the sheath and replacement of the needle into the sheath. Even more particularly, the present invention relates to a device which permits an operator to unsheath and resheath a medical needle with the use of only one hand.

2. Description of the Prior Art

In the past, a number of devices have been introduced for the handling of hypodermic syringe needles, catheter needles, or the like, for the purposes of safety and/or prevention of the spread of disease.

The simplest class of such devices is represented in several forms in U.S. Pat. No. 4,742,910 to Staebler, U.S. Pat. No. 4,717,386 to Simmons and U.S. Pat. No. 4,596,652 to Vernon. Each of these documents describe, in various degrees of complexity, hand-held medical needle sheath removal and holder devices which require an operator to grasp the device in one hand and then, with the other hand, insert the sheathed needle into the device so that the device may remove and hold the sheath. After use of the syringe, or the like, the operator reinserts the needle into the sheath which is held in the holder device. In order to then remove the sheathed needle from the holder device, the operator must again grasp the holder device with one hand and then grasp and pull the sheathed needle portion of the syringe, or the like, from the holder with the other hand. Such devices, if used properly, will usually prevent accidental pricking by the medical needle and the potential spread of disease associated therewith.

A serious drawback with such devices, however, is that they require two hands in order to properly sheath and unsheath the needle. As can be appreciated, a doctor, nurse, or other medical technician does not always have the luxury of the free use of both hands at such times when a patient must be restrained, such as, for example, when a patient is violently writhing from pain, convulsions, madness, etc. During such instances, it is quite commonly required of the person performing an injection to use one of his or her hands to restrain at least the arm of the patient. Clearly then, during such moments of medical emergency, the person performing the injection cannot exercise the care required to properly operate the aforesaid sheath removal and holder devices. And with such disregard of the proper use or even the complete avoidance of the use of such equipment during these emergencies, the risk of accidental pricking with the needle and the potential spread of disease associated therewith increase dramatically.

Another disadvantage of such prior art devices is that they are unwieldy and impractical at such times when a surgeon, dentist, or the like, performs local anesthetic administration. For example, when the dentist or surgeon is palpating for landmarks, i.e., reference sites such as bones, tissue nodes, bumps, or the like, which are used for precise positioning of the location of the injection, it is essential, especially if the landmarks are difficult to locate, that he maintain his fingers at the desired landmark or landmarks once they have been located. In this way the surgeon or dentist uses the positioning of his fingers as a guide for accurately placing the needle for injection.

However, with the prior art devices, the operator must use both hands to remove the sheath from the needle, thus requiring the operator to remove his fingers from the landmark if the landmark has already been located. If, however, the surgeon or dentist decides to first remove the sheath before palpating for landmarks, he thus leaves the needle exposed for an unduly prolonged length of time which again raises the likelihood of accidental pricking with the needle, particularly if the operator holds the syringe with one hand and palpates with the other.

Another shortcoming of the prior art needle sheath holders is that they are burdensome and may inhibit the rapid sequential administration of a number of injections of various types and quantities of drugs as is commonly performed by an anesthesiologist during a surgical operation. For example, prior to a surgical operation in which a patient is to receive general anesthesia, it is common for an anesthesiologist to prepare a number of syringes containing various concentrations and types of drugs, usually narcotics, for sequential injection into the patient through the use of a catheter. During such a procedure, it is not uncommon for various quantities of drugs from several of the syringes to be administered in relatively rapid sequence. It is also not uncommon for the anesthesiologist to use one or more of the syringes a number of times during the surgical procedure. For purposes of safety, i.e., in order to prevent accidental injection of an anesthetic into either the anesthesiologist or the other members of the surgical team, the needles of the syringes are preferably capped between usages and after their final usages. Bearing this in mind, one will appreciate that the anesthesiologist must spend a significant quantity of time and care in the unsheathing and resheathing of syringes during a surgical operation. If the surgery should become lengthy, the anesthesiologist may become fatigued and possibly neglect recapping of one more of the syringes between usages and after final usage. Along similar lines, if quantities of drugs from several of the syringes must be injected in rapid sequence, the anesthesiologist may neglect capping one syringe before using the next syringe. In either case, one or more of the needles may be left uncapped during the surgical procedure thus increasing the risk of accidental pricking of the medical personnel by the exposed needles.

A further problem exists in such a procedure. As noted previously, surgical operations may sometimes become quite lengthy and the anesthesiologist may accordingly become fatigued. It is particularly at such times when the anesthesiologist is most likely to prick the hand which holds the needle sheath even if the sheath is retained in a sheath holder. To avoid these potential problems, the anesthesiologist must somehow be able to quickly, easily and assuredly unsheath and resheath the syringe needles at a first remote, yet easily reachable location, using only one hand, while keeping the other hand a safe distance therefrom. However, such a procedure is not possible using the sheath holder devices disclosed in the aforementioned U.S. Pat. No. 4,742,910, U.S. Pat. No. 4,717,386 and U.S. Pat. No. 4,596,652.

A somewhat more advanced form of medical needle sheath remover and holder device is disclosed in European Patent No. EP 0 296 406 A1. Described therein is a device which permits an individual to: 1) remove sheaths from medical needles, or 2) remove sheathed needles from a syringe, or the like, with the use of only one hand. While this device may represent an improvement over the previously mentioned prior art as far as removing the sheaths is concerned, it fails to provide any means for permitting resheathing of a needle after an injection is completed. If one using such a device desired to resheath the needle, one would first have to physically remove the sheath from the device and then replace the sheath onto the needle by hand, thus again requiring a "two-hand" operation to resheath the needle. Hence, such a device could not be effectively used by an anesthesiologist to uncap and recap needles in rapid succession. Furthermore, such a device would be of limited utility during some instances of medical emergency since, for reasons mentioned hereinabove, the medical personnel may not have the benefit of the free use of the "second hand" to resheath the needle during such times of emergency.

An advantage exists, therefore, for a device which will:

1) permit medical personnel to quickly and positively unsheath and resheath the needles of hypodermic syringes, catheters, etc., using only one hand, and 2) reduce the likelihood of accidental pricking with the needle by allowing an individual to maintain his hands at a safe distance from one another during unsheathing and resheathing of the needle, by permitting an individual to avoid premature unsheathing of the needle, and by permitting an individual to avoid unnecessarily prolonged periods of time in which the needle remains unsheathed.

It is therefore an object of the present invention to provide a device for permitting a person to quickly and positively unsheath and resheath the needles of hypodermic syringes, catheters, etc., using only one hand thus permitting unrestricted and free use of the person's other hand before, during, and after an injection into a patient is performed.

It is a further object of the invention to provide a device which reduces the likelihood of accidental pricking by the needle by permitting an operator to avoid both premature unsheathing of the needle and unnecessarily prolonged periods of time in which the needle is unsheathed.

It is a further object of the present invention to provide a device which permits a person to unsheath and resheath a medical needle while keeping his hands a safe distance from one another during the unsheathing and resheathing operation to thus reduce the likelihood of pricking of the person's hand not carrying the needle.

It is a further object of the invention to provide a device for securely holding and positioning a sheath during and after such time that a medical needle is removed therefrom as well as when the needle is reinserted thereinto.

It is a further object of the present invention to provide a device which will permit a series of needles to be unsheathed and resheathed in rapid succession.

It is a further object of the present invention to provide a medical needle sheath holder apparatus which is of a rugged, yet uncomplicated and inexpensive construction.

Still other objects and advantages will become apparent when one considers the attached drawings and written description of the invention provided hereinbelow.

SUMMARY OF THE INVENTION

In accordance with the present invention there is provided an apparatus for permitting an individual to quickly and safely unsheath and resheath the needles of hypodermic syringes, catheters, etc., with the use of only one hand. Consequently, the present invention permits free use of the individual's other hand when such is required, e.g., when restraint of the patient is necessary in order to properly and safely administer an injection from a hypodermic needle, catheter, or the like.

The preferred embodiment apparatus of the present invention comprises a housing having a reciprocable, spring-biased base member provided therein. An actuator of a microswitch is in contact with a first side of the base member. Alternate depressions of the microswitch actuator by translation of the base member against the spring bias causes the microswitch to activate and deactivate a solenoid associated therewith. The solenoid and a needle sheath gripping means are carried on a second side of the base member so as to be translatable therewith. The needle sheath gripping means includes a plurality of parallel plate-like members each having a bore therethrough.

In a first position of the solenoid, which carries one of the plate-like members on an arm thereof, the bores of the plate-like members are in alignment to permit a sheathed needle to be inserted thereinto or removed therefrom. In a second position of the solenoid, the bore of the plate-like member which is carried on the arm of the solenoid is misaligned relative to the bores of the other plate-like members so that the misaligned bores gently yet firmly grip the needle sheath received therein. In this position, a needle can be removed from or received in the sheath while the sheath remains retained in the grip of the misaligned bores.

The aforesaid depressions of the microswitch actuator which cause the microswitch to activate and deactivate the solenoid are effected by the exertion of manual force against the second side of the base member. Normally this exerted force is transmitted through the tip of the needle sheath which engages a striker plate fixed to the second side of the base member. The force thus directed against the base member by the sheath tip translates the base member against the force of the spring bias. Alternate translations of the base member against the spring bias cause the microswitch to operate the solenoid to alternatively misalign and align the bores of the gripping means so as to respectively grip and release a needle sheath positioned therein.

The apparatus may be portable or stationary and operated by either an AC or DC power supply. Preferably, a stop member is mounted to the housing to reduce premature wear and failure of the microswitch.

DESCRIPTION OF THE PREFERRED EMBODIMENT

Figure 1:
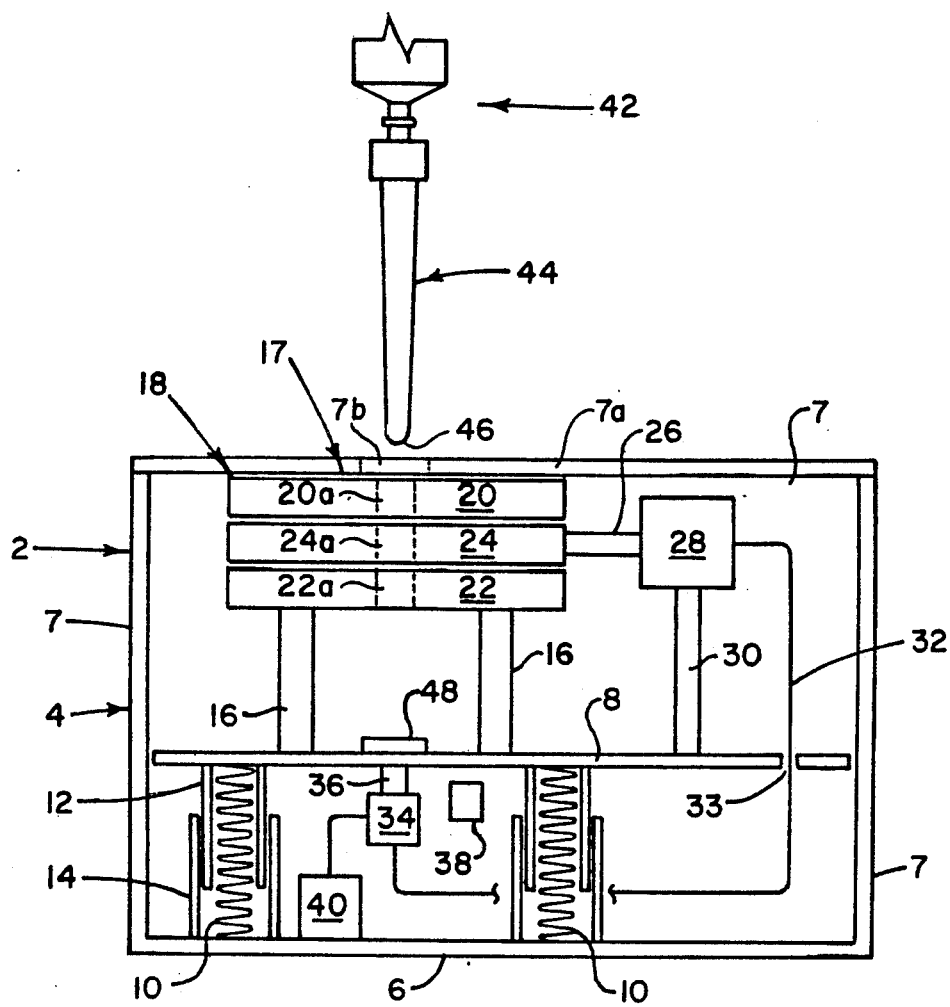
FIG. 1 is a side view of the medical needle sheath holding apparatus of the present invention with a sidewall and other elements thereof omitted for purposes of clarity.

Referring now to FIG. 1 there is depicted a side view of a medical needle sheath holding apparatus 2 constructed in accordance with the preferred embodiment of the present invention.

Sheath holding apparatus 2 includes a housing 4 having a bottom portion 6, upstanding walls 7 (only three of which are shown) and a top 7a. Reciprocably and guidingly supported within housing 4 is a base member 8. Fixed at first ends thereof to an inner or bottom side of base member 8 are a plurality of compression springs 10. At their opposite ends springs 10 are fixed to bottom portion 6 of housing 4. Each of the springs 10 is prevented from buckling and is guided during compression by virtue of its containment within tubular members 12 and 14. As will be appreciated from reference to FIGS. 1, 2, 4-6, and 8, top 7a acts as a stop for limiting upward translation of base member 8, and structure attached thereto to be described later, due to the bias of springs 10. Tubular member 12 is fixed to an inner or bottom side of base member 8 and is telescopically received in tubular member 14, itself being fixed to bottom portion 6.

Attached by support means 16 to an upper or outer surface of base member 8 is a stationary portion 17 of gripping means 18. Gripping means 18, in the preferred illustrated embodiment, includes at least three substantially parallel plate-like members 20, 22 and 24. Plate-like member 20, as can be seen in FIG. 1, normally gently contacts the undersurface of top 7a due to the bias of springs 10. It is conceivable that two such plate-like members may be used to perform the sheath-gripping operation of apparatus 2, but for reasons to be described in greater detail hereinbelow, such a design is not preferred.

Figure 9:
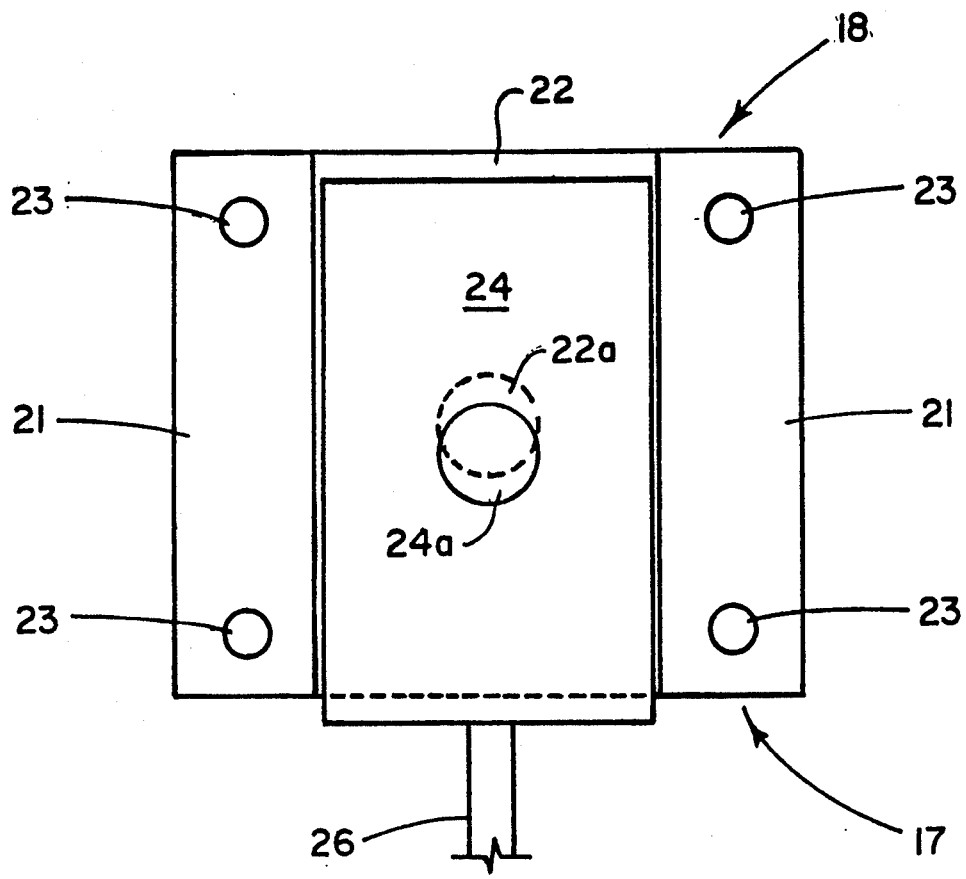
FIG. 9 is a top view, with some elements omitted for purposes of clarity, of the preferred needle sheath gripping means structure constructed in accordance with the present invention.
Figure 10:
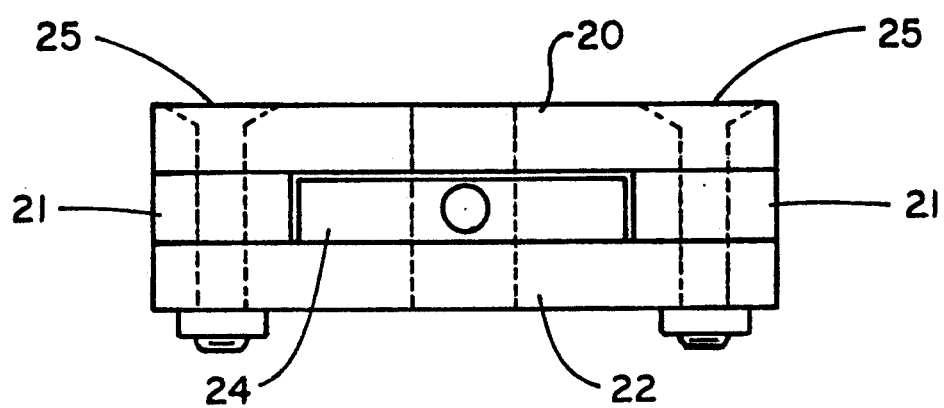
FIG. 10 is an end view of the needle sheath gripping structure illustrated in FIG. 9.

As can be seen in the drawing figures, with particular reference to FIGS. 9 and 10, plate-like members 20 and 22, which constitute the majority of the stationary portion 17 of gripping means 18, are preferably formed from separate parallel members arranged in such a manner that they are both fixed to and translatable with reciprocable base member 8 as well as being fixed in relation to one another. Plate-like member 24, which forms the movable portion of gripping means 18, is positioned between plate-like member 20 and 22. FIG. 9 illustrates the gripping means 18 in a "gripping" position which is described in greater detail hereinbelow.

As can be most clearly seen in FIG. 10, upper plate-like member 20 is spaced from lower plate-like member 22 by a pair of lateral spacer bars 21 which also form part of the stationary portion 17. Spacer bars 21 serve as lateral guides for plate-like member 24 as it reciprocates relative to the stationary portion 17, the operation of which is described hereinbelow. Plate-like members 20, 22 and spacer bars 21 are each provided with a plurality of holes 23 which are alignable with one another to receive a plurality of preferably removable fasteners 25, such as screws or bolts, for rigidly fastening plate-like members 20, 22 to one another and also to spacer bars 21. With such a construction plate-like member 24 is constrained by the inner surfaces of plate-like members 20, 22 and the inner surfaces of spacer bars 21 to reciprocate in a smooth linear fashion. Moreover, for smooth operation, the outer surfaces of reciprocable plate-like member 24 and/or the inner surfaces of plate-like members 20, 22 and spacer bars 21 in contact therewith may be coated with a friction reducing coating such as teflon, or the like.

Circular bores 20a, 22a and 24a are provided in plate-like members 20, 22 and 24, respectively. These bores are of sufficient diameter to accommodate the largest conventional needle or catheter sheaths such that when in alignment, they permit any conventional sheathed needle or catheter to be inserted therein or removed therefrom in a convenient linear stroke-like motion. Also, since most medical needle sheaths are substantially square in cross-section, a person inserting a sheathed needle into the circular bores does not have to first orient the sheath with the shape of the bores before inserting the sheath therein.

An arm 26 is attached at a first end thereof the plate-like member 24 and at a second end thereof to a reciprocable actuator such as solenoid 28. Solenoid 28 is fixedly secured to base member 8 via support 30 so as to be translatable with base member 8. For purposes of compactness, electrical line 32 may be extended through a passageway in support 30, if desired. An electrical line 32 connected to solenoid 28 passes through an aperture 33 provided in base member 8. At its opposite end electrical line 32 is connected to microswitch 34 which, in turn, is fixed to housing 4. An actuator 36 extending from microswitch 34 extends to, and preferably contacts, the inner or bottom side of base member 8.

Downward or inward translation of base member 8 is limited by contact of the inner side of the base member with stop member 38 which is preferably adjustably fixed to a wall 7 of housing 4. The purpose of stop member 38 is to limit excessive compression of microswitch actuator 36 to thereby prevent premature wear and failure of microswitch 34.

Power for operating for medical needle sheath holding apparatus 2 is provided by power source 40 which is connected to microswitch 34. It is contemplated that power source 40 may either be an AC or DC power source depending, inter alia, on the degree of portability required of the needle sheath holding apparatus 2.

Although not illustrated, it is contemplated that other suitable means, such as pneumatic or hydraulic pressure, vacuum, or the like, may be used for reciprocating plate-like member 24. For example, if pneumatic pressure is used, power source 40 in this instance would supply pressurized air from an external source which, in turn, would serve as a pressurized air source for a reciprocable pneumatic actuator connected to arm 26. Microswitch 34 would be replaced by a suitable two-position valve which would either supply pressurized air to or exhaust pressurized air from an air line communicating the compressed air with the reciprocable pneumatic actuator. The reciprocable actuator, like solenoid 28, would normally be biased to a position in which the bores 20a, 22a and 24a are in alignment, i.e., a non-gripping position. As discussed above with regard to the actuation of microswitch 34, an actuator, similar to actuator 36, would be operably connected to the two-position valve such that alternate inward translations of the base member 8 would cause the two-position valve to perform the aforesaid supplying or exhausting of pressurized air to the pneumatic actuator. When supplied with pressurized air, the pneumatic actuator will move arm 26 and, hence, plate like member 24 to a gripping position; and when exhausted of pressurized air, the pneumatic actuator will move arm 26 to the non-gripping position.

The reader will appreciate that analogous arrangements may be created for hydraulic pressure systems, vacuum systems, or other possible alternative systems, in order to effectively translate plate-like member 24 relative to plate-like members 20 and 22 so as to urge the gripping means 18 either into or out of gripping position.

Continuing with the description of FIG. 1 there can be seen represented by element 42 a hypodermic syringe, catheter, or the like, the needle of which is covered by a sheath 44 which, as noted previously, is usually of a square outer cross-section. At the lower portion of sheath 44 is a tip 46 for contacting a striker plate 48 attached to the outer or upper side of base member 8 as will be described in greater detail hereinbelow.

Figure 8:
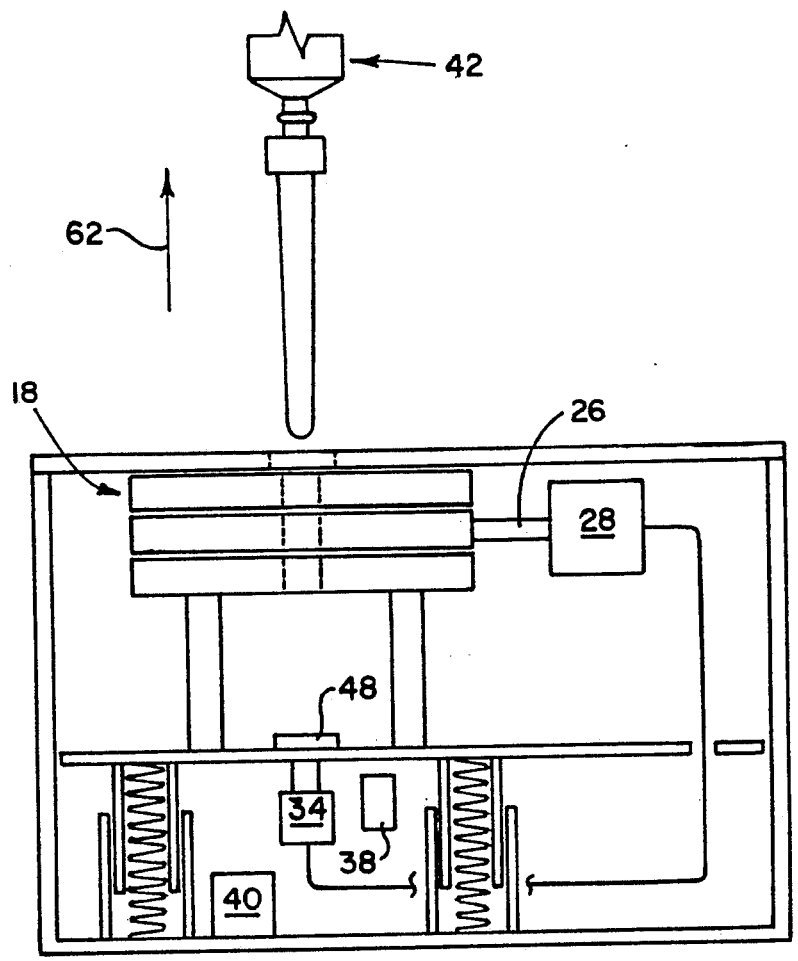

Operation of the medical needle sheath holding apparatus to will now be discussed with reference to the sequential illustrations of FIG. 2, through FIG. 8.

Figure 2:
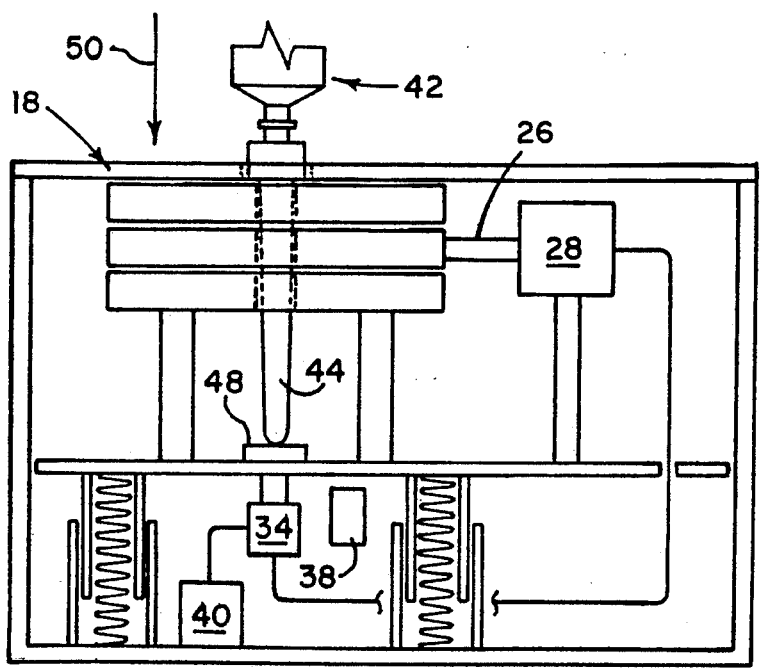
FIG. 2 through FIG. 8 illustrate along with FIG. 1, a typical sequential operation of the medical needle sheath holding apparatus of the present invention.

As can be seen in FIG. 2, bores 20a, 22a and 24a of plate-like members 20, 22 and 24 are in alignment with one another as well as with a bore 7b in top 7a which is of somewhat larger diameter than bores 20A and 22A. Such a condition, for purposes of discussion only, will hereinafter be referred to as representing a "deactivated" condition of solenoid 28 and gripping means 18. When bores 20a, 22a and 24a are aligned, the sheathed syringe or catheter 42 is then inserted in the direction of arrow 50 into the aligned bores until the tip 46 of the sheath 44 contacts the upper or outer surface of striker plate 48. Striker plate 48 is of sufficient height or is adjustable thereto, or, alternatively, support means 16 and support 30 may be of a preselected minimum height or adjustable thereto, such that the tip 46 of any conventional medical needle sheath inserted in the aligned bores will contact the striker plate 48, regardless of the length of the sheath.

Figure 3:
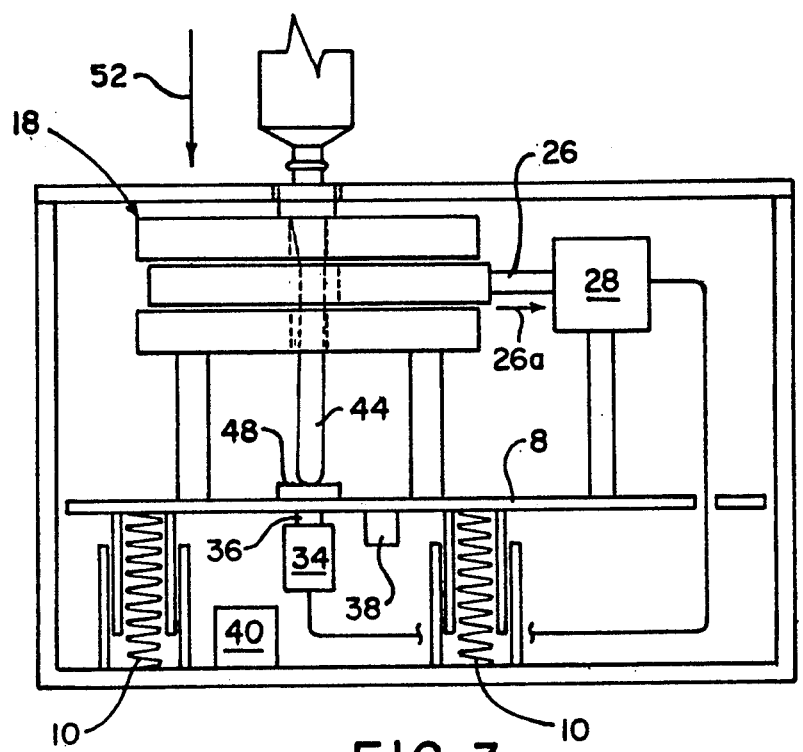

Proceeding to FIG. 3, it can be seen that continued force exerted by the catheter or syringe 42 in the direction of arrow 52 causes the tip 46 of the sheath to displace the gripping means 18 and, hence, base member 8 downwardly or inwardly against the bias of springs 10 Displacement of the base member 8 causes a corresponding displacement of the microswitch actuator 36 to the level of the outer surface of stop means 38 which, in turn, causes the microswitch 34 to activate the solenoid 28. Actuation of the solenoid 28 displaces the arm 26 and thereby movable plate-like member 24 of gripping means 18 in the direction of arrow 26a. In such a position the gripping means 18 is considered to be in an "activated" condition. It will be appreciated that the solenoid 28 may be activated to move the plate-like member 24 in a direction opposite to or substantially lateral to arrow 26a, if so desired, so long as the solenoid causes the bore 24a to become displaced relative to bores 20a and 22a in a manner similar to that depicted in FIG. 3. Moreover, the degree of displacement of bore 24a relative to bores 20a and 22a is preferably adjustable to gently yet firmly hold sheaths 44 of various sizes while avoiding bending or shearing of the needles encased within the sheaths. Moreover, as aforementioned, bores 20a, 22a, and 24a are preferably circular in order to positively engage the usually square periphery of the sheath 44 and, at the same time, such circular bores eliminate any need for an operator to positively and deliberately align the outer cross-section of the sheath in the aligned bores before it is placed therein.

As mentioned hereinabove, it is contemplated that only two plate-like members rather than three may be used in the sheath holding apparatus, if desired. Such a situation is not preferred since the movable plate-like member, when displaced, will tend to tilt the hypodermic needle or syringe 42 when received it is in the apparatus 2. Moreover, it is not believed that the provision of only two plate-like members will hold a sheath as securely as the three plate system disclosed herein at such times when the needle is to be inserted in or removed from the sheath.

Figure 4:
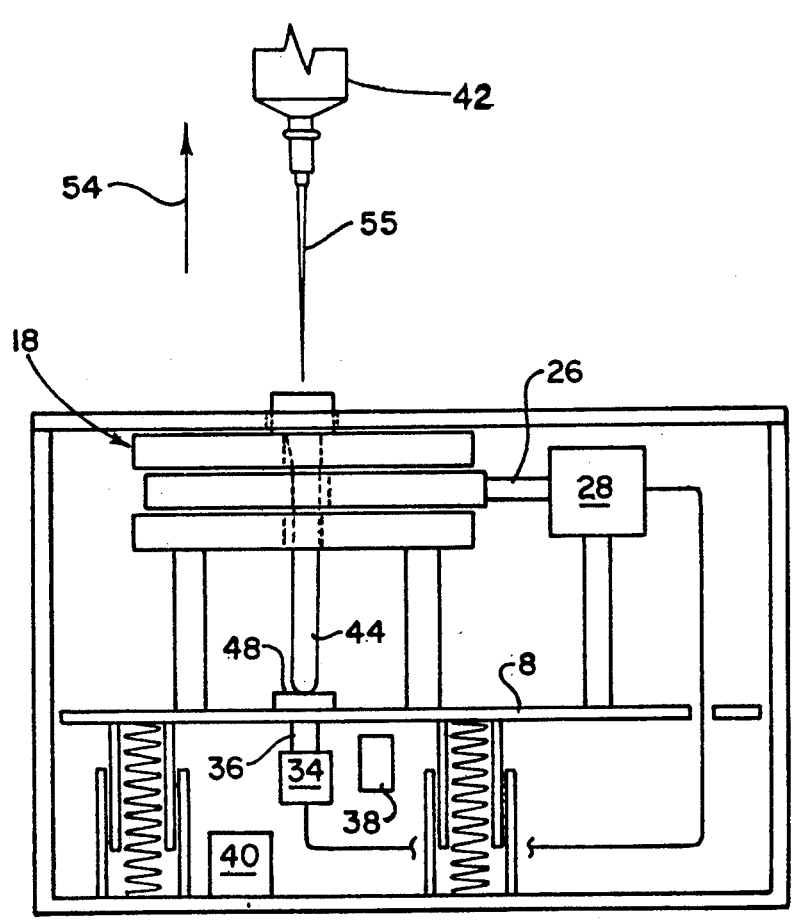

With reference now to FIG. 4, it can be seen that with the sheath 44 now firmly held in gripping means 18, the syringe or catheter 42 and the needle 55 attached thereto can be removed from apparatus 2 by exerting a force on the syringe or catheter 42 in the direction indicated by arrow 54. This, in turn, permits the biasing force in springs 10 to return base member 8 to its initial level and the upper surface of plate-like member 20 into gentle contact with the undersurface of top 7a. At such time, microswitch actuator 36 also returns to its initial "extended" position.

FIGS. 1 through 4, therefore, graphically illustrate the unsheathing of a needle 55 of a hypodermic syringe, a catheter 42, or the like, using the novel needle sheath holder apparatus 2 of the present invention. FIGS. 5 through 8, to be described hereinbelow, depict the resheathing of needle 55.

Figure 5:
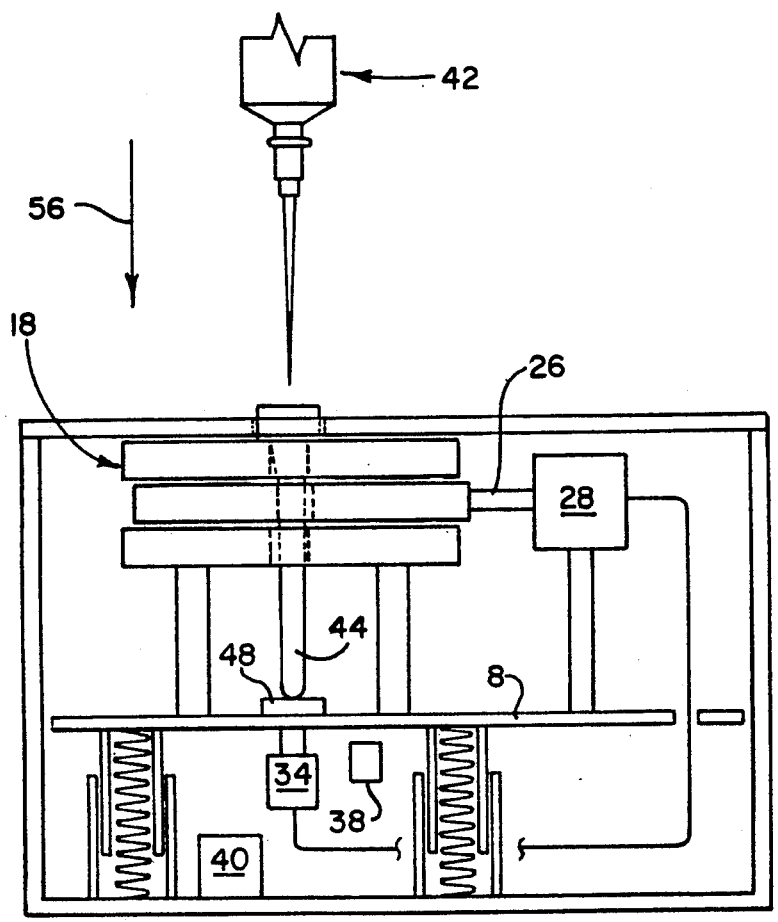
Figure 6:
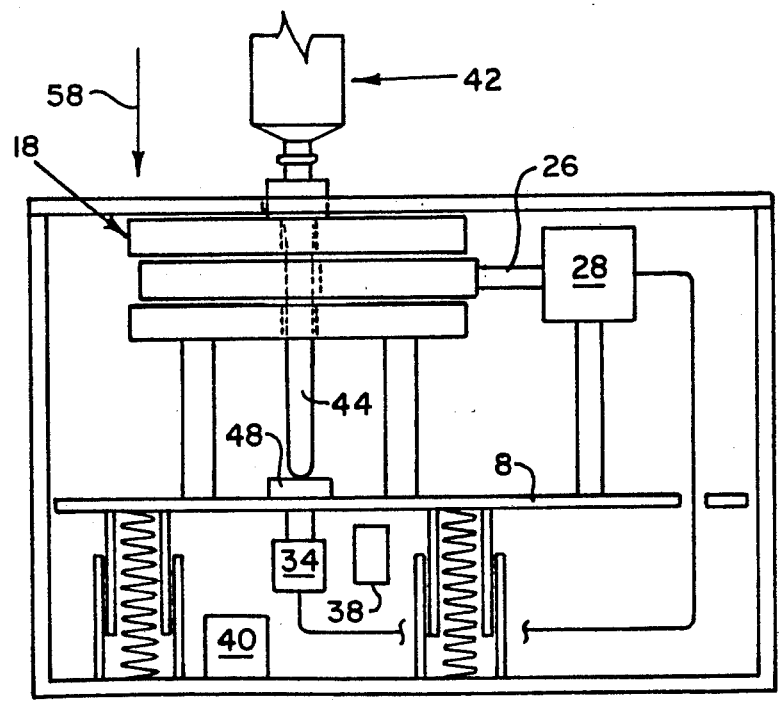
Figure 7:
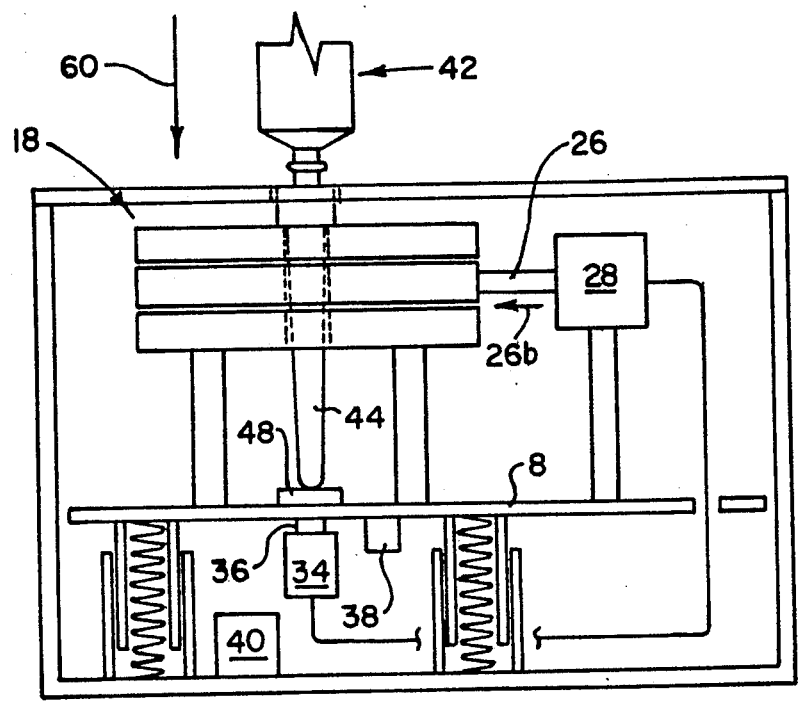

FIG. 5 is substantially identical to FIG. 4 except it will now be appreciated that the syringe or catheter 42 has been used and needle 55 is about to be resheathed. Accordingly, syringe or catheter 42 is inserted in the direction indicated by arrow 56 (FIG. 5) and arrow 58 (FIG. 6) into the sheath 44 which is retained in gripping means 18. Continued downward force exerted by the syringe or catheter 42 in the direction of arrow 60 (FIG. 7) once again displaces base member 8 against the force of biasing springs 10 until the base member contacts stop means 38. As before, the microswitch actuator 36 is correspondingly displaced to thereby cause the microswitch 34 to "deactivate" the solenoid 28. Deactivation of solenoid 28 moves plate-like member 24 in the direction indicated by arrow 26b to realign bores 20a, 22a and 24a as seen in FIG. 7. At this time, the resheathed needle 55 and its syringe or catheter 42 may be removed from apparatus 2 by pulling the catheter or syringe in the direction indicated by arrow 62 in FIG. 8. Accordingly, base member 8 reattains its initial level due to the bias of springs 10, and microswitch actuator 36 is similarly returned to its initial extended condition. The configuration of FIG. 8 is identical to FIG. 1 and the medical needle sheath holder apparatus 2 of the present invention is prepared to again unsheath a catheter or syringe needle.

While not illustrated, it is contemplated that housing 4 may be fixed to any horizontal or inclined surface by suitable conventional hardware. Moreover, the apparatus 2 may be completely portable in which case it has particular advantageous application for field usage by emergency medical personnel such as paramedics.

The major components of the apparatus 2, i.e., housing 4, base member 8 and plate-like members 20, 22 and 24 may be formed of durable plastic, metal, or the like.

From the foregoing, one skilled in the art will appreciate that the medical needle sheath holder apparatus of the present invention permits an individual to safely and positively unsheath and resheath hypodermic syringe needles, catheter needles, or the like, by using only one hand thus permitting the individual to use his or her free hand for other important activities.

While the present invention has been described in accordance with the preferred embodiments of the various figures, it is to be understood that other similar embodiment may be used or modifications and additions may be made to the described embodiment for performing the same functions of the present invention without deviating therefrom. Therefore, the present invention should not be limited to any single embodiment but rather construed in breadth and scope in accordance with the recitation of the appended claims.

I claim:

1. Apparatus for holding a sheath during unsheathing and resheathing of a needle or catheter, said apparatus permitting a user to perform said unsheathing and resheathing using one hand in a convenient linear stroke-like motion, said apparatus comprising:
   means for gripping said sheath, said gripping means being positionable to an operative sheath-gripping position and an inoperative non-gripping position; and
   actuator means controlled by a sensor for positioning said gripping means into said operative and inoperative positions,
   whereby said apparatus, when said gripping means are in said operative position, gently yet firmly holds said sheath so that the needle or catheter can be inserted into and removed from the sheath, and, when said gripping means are in said inoperative position, a sheathed needle or catheter be can be inserted into and removed from said apparatus.

2. The apparatus of claim 1 wherein said gripping means comprise a stationary portion and a movable portion.

3. The apparatus of claim 2 further including at least one bore provided in each of said stationary portion and said movable portion,
   whereby when said at least one bore of said stationary portion and said at least one bore of said movable portion are in alignment said gripping means are considered to be in said inoperative position, and, when said at least one bore of said stationary portion and said at least one bore of said movable portion are in misalignment said gripping means are considered to be in said operative position.

4. The apparatus of claim 3 wherein said means for positioning comprise means for displacing said movable portion relative to said stationary portion in order to attain said operative and inoperative positions of said gripping means.

5. The apparatus of claim 4 wherein said actuator means comprises a reciprocable actuator and said sensor controls said reciprocable actuator in response to said insertion of a needle or catheter into said gripping means.

6. The apparatus of claim 5 further comprising a housing, said reciprocable actuator comprises a solenoid having an arm attached to said movable portion, and said sensor comprises a microswitch connected to said housing and electrically connected to said solenoid for activation and deactivation of said solenoid in order to translate said movable portion and an electrical power source electrically connected to said microswitch.

7. The apparatus of claim 6 further comprising a reciprocally displaceable base member for supporting said gripping means, said base member being operatively connected to said microswitch and displaceable by said insertion of a needle or catheter into said gripping means,
   wherein alternate displacements of said base member operate said microswitch and cause alternative activation and deactivation of said solenoid to alternately position said gripping means into said operative and inoperative positions.

8. The apparatus of claim 7 further comprising means situated between said housing and said base member for biasing said base member to a non-displaced initial position.

9. The apparatus of claim 3 wherein said stationary portion and said movable portion each comprise at least one plate-like member, said plate-like members being substantially parallel to one another.

10. The apparatus of claim 9 wherein said stationary portion comprises first and second spaced parallel plate-like members and said movable portion comprises a third plate-like member situated between said first and second plate-like members.

11. The apparatus of claim 10 wherein said first plate-like member of said stationary portion is provided with a bore and said second plate-like member of said stationary portion is provided with a bore, said bores of said first and second plate-like members of said stationary portion at all times remaining in alignment with one another.

12. Apparatus for holding a sheath during unsheathing and resheathing of a needle or catheter, said apparatus permitting a user to perform said unsheathing and resheathing using one hand in a convenient linear stroke-like motion, said apparatus comprising:
   means for gripping said sheath, said gripping means being positionable to an operative sheath-gripping position and an inoperative non-gripping position; and
   means responsive to insertion of said needle or catheter into said gripping means for positioning said gripping means into said operative and inoperative positions,
   whereby said apparatus, when said gripping means are in said operative position, gently yet firmly holds said sheath so that the needle or catheter can be inserted into and removed from the sheath, and, when said gripping means are in said inoperative position, a sheathed needle or catheter be can be inserted into and removed from said apparatus.

* * * * *